United States Patent
Klaveness et al.

(10) Patent No.: US 6,177,061 B1
(45) Date of Patent: Jan. 23, 2001

(54) CONTRAST AGENTS COMPRISING AN AZEOTROPIC MIXTURE OF TWO GASES FOR ULTRASOUND INVESTIGATIONS

(75) Inventors: Jo Klaveness; Roald Skurtveit; Pål Rongved; Lars Hoff, all of Olso (NO)

(73) Assignee: Nycomed Imaging AS, Oslo (NO)

( * ) Notice: Under 35 U.S.C. 154(b), the term of this patent shall be extended for 0 days.

(21) Appl. No.: 09/422,323

(22) Filed: Oct. 21, 1999

Related U.S. Application Data

(63) Continuation of application No. PCT/GB98/01185, filed on Apr. 23, 1998.
(60) Provisional application No. 60/044,405, filed on Apr. 29, 1997.

(30) Foreign Application Priority Data

Apr. 23, 1997 (GB) .................................................. 9708240

(51) Int. Cl.⁷ .................................................. A61B 5/055
(52) U.S. Cl. .................... 424/9.51; 424/9.52; 600/431
(58) Field of Search ............................... 424/9.52, 9.51; 600/431; 500/411; 252/67; 62/114

(56) References Cited

U.S. PATENT DOCUMENTS

| | | | |
|---|---|---|---|
| 5,556,610 * | 9/1996 | Yan et al. ............................ | 424/9.52 |
| 5,605,882 * | 2/1997 | Klug et al. ........................... | 510/411 |
| 5,607,616 * | 3/1997 | Minor et al. ......................... | 252/67 |
| 5,614,565 * | 3/1997 | Werner et al. ....................... | 521/131 |
| 5,639,443 * | 6/1997 | Schutt et al. ........................ | 424/9.52 |

FOREIGN PATENT DOCUMENTS

| | | |
|---|---|---|
| WO 94 16739 | 8/1994 | (WO) . |
| WO 95 02652 | 1/1995 | (WO) . |
| WO 95 03835 | 2/1995 | (WO) . |
| WO 95 16467 | 6/1995 | (WO) . |
| WO 96 08234 | 3/1996 | (WO) . |
| WO 96 26746 | 9/1996 | (WO) . |
| WO 96 39197 | 12/1996 | (WO) . |

* cited by examiner

*Primary Examiner*—Gary E. Hollinden
(74) *Attorney, Agent, or Firm*—Bacon & Thomas

(57) ABSTRACT

A contrast agent for use in diagnostic studies, particularly ultrasound imaging, comprising a dispersion in an injectable aqueous medium of a biocompatible azeotropic mixture which is in gaseous form at 37° C., at least one component of said mixture being a halocarbon having a molecular weight of at least 100.

12 Claims, No Drawings

CONTRAST AGENTS COMPRISING AN AZEOTROPIC MIXTURE OF TWO GASES FOR ULTRASOUND INVESTIGATIONS

This application is a continuation of pending international application number PCT/GB98/01185 filed Apr. 23, 1998 (of which the entire disclosure of the pending, prior application is hereby incorporated by reference), which itself is a continuation-in-part of U.S. provisional application Ser. No. 60/044,405 filed Apr. 29, 1997.

This invention relates to diagnostic imaging, more particularly to novel contrast agent preparations and their use in ultrasound imaging.

It is well known that ultrasound imaging constitutes a potentially valuable diagnostic tool, for example in studies of the vascular system and tissue microvasculature, particularly in cardiography. A variety of contrast agents has been proposed to enhance acoustic images so obtained, including suspensions of solid particles, emulsified liquid droplets, gas bubbles and encapsulated gases or liquids. It is generally accepted that low density contrast agents which are easily compressible are particularly efficient in terms of the acoustic backscatter they generate, and considerable interest has therefore been shown in gas-containing and gas-generating systems.

Over about the last five years particular attention has been focussed on the selection of gases and gas mixtures which exhibit enhanced stability and therefore longer-lasting contrast effects in vivo compared to the hitherto most commonly used gases such as air and components thereof, for example nitrogen, oxygen and carbon dioxide. Thus, for example, in WO-A-9305819 there is proposed the use of dispersions of free microbubbles of gases having a coefficient Q greater than 5 where $$Q=4.0\times10^{-7}\times\rho/C_s D$$

(in which $\rho$ is the density of the gas in kg.m$^{-3}$, $C_s$ is the water solubility of the gas in moles.l$^{-1}$ and D is the diffusivity of the gas in solution in cm$^3$.sec$^{-1}$). An extensive list of gases said to fulfil this requirement is presented, including fluorine-containing gases such as sulphur hexafluoride and various fluorocarbons. It is noted that significant echogenicity is observed only for dispersions of gaseous materials; thus, for example, in vitro experiments at 37° C. showed an aqueous dispersion of perfluoropentane (b.p. 29.5° C.) to be highly echogenic, whereas a similar dispersion of perfluorohexane (b.p. 59–60° C.), which has an approximately 8-fold greater Q-coefficient, was undetectable by ultrasound scanning under the same conditions.

In EP-A-0554213 it is suggested that one may impart resistance against collapse under pressure to gas-filled microvesicles by introduction thereto of at least one gas whose solubility in water, expressed in liters of gas/liter of water under standard conditions, divided by the square root of its molecular weight does not exceed 0.003. Preferred gases are said to include sulphur hexafluoride, selenium hexafluoride and various Freons®.

In WO-A-9503835 there is proposed the use of membrane-encapsulated microbubbles containing a gas mixture having a composition based on considerations of gas partial pressures both inside and outside the microbubbles, so as to take account of osmotic effects on microbubble size. Representative mixtures comprise a gas having a low vapour pressure and limited solubility in blood or serum (e.g. a fluorocarbon) in combination with another gas which is more rapidly exchanged with gases present in normal blood or serum (e.g. nitrogen, oxygen, carbon dioxide or mixtures thereof); the fluorocarbon or like gas preferably has a molecular weight at least four times that of the more rapidly exchanged gas.

In WO-A-9516467 there is suggested the use of ultrasound contrast media containing a surfactant-stabilised mixture of gases A and B, where gas B is present in an amount of 0.5–41% v/v, has a molecular weight greater than 80 daltons and has an aqueous solubility of less than 0.0283 ml/ml water under standard conditions, the balance of the mixture being gas A, which may comprise one or more gases with molecular weights below 80 daltons. Representative gases A include air, oxygen, nitrogen, carbon dioxide and mixtures thereof. Representative gases B include fluorine-containing gases such as sulphur hexafluoride and various perfluorinated hydrocarbons. It is postulated that the high molecular weight gas B has the effect of "plugging holes" in the encapsulating membranes at the microbubble boundaries, thereby preventing escape by transmembrane diffusion of the low molecular weight gas A.

Gas-generating ultrasound contrast agents comprising colloidal liquid-in-liquid dispersions in which the dispersed phase comprises a volatile liquid having a boiling point below the body temperature of the subject to be imaged (typically 37–40° C.) are described in WO-A-9416739; such phase shift colloids are said to exhibit excellent storage stability while generating highly echogenic microbubbles following administration. Preferred dispersed phase liquids include fluorine-containing chemicals such as perfluoropentane. It is stated that the dispersed phase may also be selected from azeotropic mixtures having a boiling point at or below the body temperature of the subject; acetone-pentane, ethyl ether-isoprene, ethyl ether-methyl formate, ethyl ether-water, isoprene-(2-methylbutane), isopropyl chloride-water, methyl vinyl chloride-water, pentane-water, vinyl ethyl ether-water, acetone-isoprene-water, carbon disulphide-methanol-methyl acetate and carbon disulphide-methanol-methylal azeotropic mixtures are described by way of example.

Such azeotropic mixtures would not in practice be expected to give long-lasting contrast effects in vivo in view of the relatively high water solubilities and relatively low molecular weights (in all cases less than 80) of the components. Moreover, phase shift colloids in general have been found to exhibit a number of potentially disadvantageous properties. Thus some workers have suggested that their administration may lead to generation of microbubbles which grow uncontrollably and unevenly, possibly to the extent where at least a proportion of the microbubbles may cause potentially dangerous embolisation, for example of the myocardial vasculature and brain (see e.g. Schwarz, *Advances in Echo-Contrast* [1994(3)], pp. 48–49). Others have found that administration of phase shift colloids may not lead to reliable or consistent volatilisation of the dispersed phase in vivo. Thus Grayburn et al. in *J. Am. Coll. Cardiol.* 26(5) [1995], pp. 1340–1347 suggest that preactivation of perfluoropentane emulsions may be required to achieve myocardial opacification in dogs if doses low enough to avoid haemodynamic side effects are to be effective. An activation technique for such colloidal dispersions, involving application of hypobaric forces thereto, is described in WO-A-9640282; this typically involves partially filling a syringe with the emulsion and subsequently forcibly withdrawing and then releasing the plunger of the syringe to generate a transient pressure change which causes formation of gas microbubbles within the emulsion: clearly this is an inherently somewhat cumbersome technique which may fail to give consistent levels of activation.

The present invention is based on the finding that contrast agents comprising halocarbon-containing azeotropic mixtures in which the halocarbon has a molecular weight of at least 100 exhibit a number of useful and advantageous properties. Thus, for example, azeotrope formation may be used effectively to enhance the volatility of relatively high molecular weight halocarbons which under standard conditions are liquid at the normal human body temperature of 37° C., such that they may be administered in gaseous form at this temperature. This has substantial benefits as regards the effective echogenic lifetime in vivo of contrast agents containing such azeotropic mixtures since, as is apparent from the prior art discussed above, parameters such as the water solubility and diffusibility of halocarbons decrease with increasing molecular weight and size, as does their fat solubility.

Azeotrope formation may similarly be used where appropriate to generate mixtures which are gaseous at normal room and storage temperatures (e.g. 15–20° C.) despite containing halocarbons which in isolation have boiling points above such temperatures. Contrast agents containing such mixtures may be administered directly to a subject without any need for heating or other forms of activation to avoid phase shift effects upon administration. Moreover, lowering of the boiling point of the gas content of contrast agents by azeotrope formation, e.g. to a temperature of 0–15° C. or less, may permit use of relatively low temperatures during manufacture and storage of the contrast agents while avoiding liquefaction of the gas content which might be detrimental to the structure of the agents.

In general, the recognised natural resistance of azeotropic mixtures to separation of their components will enhance the stability of contrast agents containing the same, both during preparation, storage and handling and following administration.

It will be appreciated that azeotropes useful in accordance with the invention are mixtures which exhibit a positive deviation from Raoult's law, i.e. are mixtures which have higher vapour pressures and thus lower boiling points than any of their individual components. Such positive azeotropes in many instances also exhibit lowered freezing points relative to their individual components; such depression of the freezing point may be advantageous in avoiding unwanted solidification of the gas content of contrast agents during low temperature procedures such as freeze drying which may be used in their preparation, for example as described in further detail hereinafter.

According to one aspect of the present invention there is provided a contrast agent for use in diagnostic studies, particularly ultrasound imaging, comprising a dispersion in an injectable aqueous medium of a biocompatible azeotropic mixture which is in gaseous form at 37° C., at least one component of said mixture being a halocarbon having a molecular weight of at least 100.

According to a further aspect of the invention there is provided a method of generating enhanced ultrasound images of a human or non-human animal subject which comprises the steps of:
i) injecting an ultrasound contrast agent comprising a dispersion in an injectable aqueous medium of a biocompatible gaseous azeotropic mixture into the vascular system of said subject, at least one component of said mixture being a halocarbon having a molecular weight of at least 100 and said mixture having a boiling point of less than 37° C.; and
ii) generating an ultrasound image of at least a part of said subject.

It will be appreciated that administration of the dispersed azeotropic mixture in gaseous form avoids the potential disadvantages of either excessive microbubble growth or incomplete volatilisation of the dispersed phase associated with the administration of phase shift colloids.

Halocarbons which may be present in azeotropic mixtures used in contrast agents according to the invention should contain at least one halogen atom, e.g. fluorine, chlorine, bromine or iodine. Non-halogen atoms which may be present include hydrogen and oxygen; the latter may, for example, be present in ketone or ether groups. At least a proportion, and if desired all, of the halogen atoms may advantageously be fluorine atoms; the halocarbon may thus, for example, be a perfluorocarbon. Representative examples of halocarbons having a molecular weight of at least 100 include 1,1,1-trichloroethane, trichloroethene, 1,1-dichloropropene, 2,3-dichloropropene, bromochlorodifluoromethane, dichlorodifluoromethane, bromotrifluoromethane, chlorotrifluoromethane, chloropentafluoroethane, dichlorotetrafluoroethanes, trichlorotrifluoroethanes such as 1,1,2-trichloro-1,2,2-trifluoroethane, 2-bromo-2-chloro-1,1,1-trifluoroethane (halothane), chlorotrifluoroethylene, perfluorocarbons (e.g. perfluoroalkanes such as perfluoroethane, perfluoropropanes, perfluorobutanes, perfluoropentanes, perfluorohexanes or perfluoroheptanes; perfluoroalkenes such as perfluoropropene, perfluorobutenes, perfluorobutadiene, perfluoropentenes (e.g. perfluoropent-1-ene) or perfluoro-4-methylpent-2-ene; perfluoroalkynes such as perfluorobut-2-yne; and perfluorocycloalkanes such as perfluorocyclobutane, perfluoromethylcyclobutane, perfluorodimethylcyclobutanes, perfluorotrimethylcyclobutanes, perfluorocyclopentane, perfluoromethylcyclopentane, pefluorodimethylcyclopentanes, perfluorocyclohexane, perfluoromethylcyclohexane or perfluorocycloheptane), fluorinated (e.g. perfluorinated) ketones such as perfluoroacetone, and fluorinated (e.g. perfluorinated) ethers such as perfluorodiethyl ether or perfluorocarbon ether hydrides such as are disclosed in WO-A-9531965, the contents of which are incorporated herein by reference.

The other component or components of azeotropic mixtures used in contrast agents according to the invention may, for example, be selected by reference to literature relating to azeotropes, by experimental investigation and/or by theoretical predictions, e.g. as described by Tanaka in *Fluid Phase Equilibria* 24 (1985), pp. 187–203, by Kittel, C. and Kroemer, H. in Chapter 10 of Thermal Physics (W. H. Freeman & Co., New York, USA, 1980) or by Hemmer, P. C. in Chapters 16–22 of Statistisk Mekanikk (Tapir, Trondheim, Norway, 1970), the contents of which are incorporated herein by reference.

One literature example of an azeotrope which effectively reduces the boiling point of the higher molecular weight component to below normal body temperature is the 57:43 w/w mixture of 1,1,2-trichloro-1,2,2-trifluoromethane (b.p. 47.6° C.) and 1,2-difluoromethane (b.p. 29.6° C.) described in U.S. Pat. No. 4,055,049 as having an azeotropic boiling point of 24.9° C. Other examples of halocarbon-containing azeotropic mixtures are disclosed in U.S. Pat. No. 5,599,783, U.S. Pat. No. 5,605,647, U.S. Pat. No. 5,605,882, U.S. Pat. No. 5,607,616, U.S. Pat. No. 5,607,912, U.S. Pat. No. 5,611,210, U.S. Pat. No. 5,614,565 and U.S. Pat. No. 5,616,821, the contents of which are incorporated herein by reference.

Simons et al. in *J. Chem. Phys.* 18(3) (1950), pp. 335–346 report that mixtures of perfluoro-n-pentane (b.p. 29° C.) and n-pentane (b.p. 36° C.) exhibit a large positive deviation from Raoult's law; the effect is most pronounced for approximately equimolar mixtures. In practice the boiling point of the azeotropic mixture has been found to be about 22° C. or less. Mixtures of perfluorocarbons and unsubstituted hydrocarbons may in general exhibit useful azeotropic properties; strong azeotropic effects have been observed for mixtures of such components having substantially similar boiling points. Examples of other perfluorocarbon:hydrocarbon azeotropes include mixtures of perfluoro-n-hexane (b.p. 59° C.) and n-pentane, where the azeotrope has a boiling point between room temperature and 35° C., and of perfluoro-4-methylpent-2-ene (b.p. 49° C.) and n-pentane, where the azeotrope has a boiling point of approximately 25° C.

Other potentially useful azeotropic mixtures include mixtures of halothane and diethyl ether and mixtures of two or more fluorinated gases, for example perfluoropropane and fluoroethane, perfluoropropane and 1,1,1-trifluoroethane, or perfluoroethane and difluoromethane.

It is known that fluorinated gases such as perfluoroethane may form azeotropes with carbon dioxide (see e.g. WO-A-9502652). Accordingly, administration of contrast agents containing such gases may lead to in vivo formation of ternary or higher azeotropes with blood gases such as carbon dioxide, thereby further enhancing the stability of the dispersed gas.

The dispersed azeotropic gas mixture in contrast agents according to the invention will normally be associated with some form of stabilising material such as an encapsulating membrane or a surrounding matrix. Representative examples of contrast agent formulations which may be used include microbubbles of the azeotropic gas mixture stabilised (e.g. at least partially encapsulated) by a coalescence-resistant surface membrane (for example gelatin, e.g. as described in WO-A-8002365), a filmogenic protein (for example an albumin such as human serum albumin, e.g. as described in U.S. Pat. No. 4,718,433, U.S. Pat. No. 4,774,958, U.S. Pat. No. 4,844,882, EP-A-0359246, WO-A-9112823, WO-A-9205806, WO-A-9217213, WO-A-9406477 or WO-A-9501187), a polymer material (for example a synthetic biodegradable polymer as described in EP-A-0398935, an elastic interfacial synthetic polymer membrane as described in EP-A-0458745, a microparticulate biodegradable polyaldehyde as described in EP-A-0441468, a microparticulate N-dicarboxylic acid derivative of a polyamino acid—polycyclic imide as described in EP-A-0458079, or a biodegradable polymer as described in WO-A-9317718 or WO-A-9607434), a non-polymeric and non-polymerisable wall-forming material (for example as described in WO-A-9521631), or a surfactant (for example a polyoxyethylene-polyoxypropylene block copolymer surfactant such as a Pluronic, a polymer surfactant as described in WO-A-9506518, or a film-forming surfactant such as a phospholipid, e.g. as described in WO-A-9211873, WO-A-9217212, WO-A-9222247, WO-A-9428780, WO-A-9503835 or WO-A-9729783).

Other useful gas-containing contrast agent formulations include gas-containing solid matrix systems, for example microparticles (especially aggregates of microparticles) having the azeotropic gas mixture contained therewithin or otherwise associated therewith (for example being adsorbed on the surface thereof and/or contained within voids, cavities or pores therein, e.g. as described in EP-A-0122624, EP-A-0123235, EP-A-0365467, WO-A-9221382, WO-A-9300930, WO-A-9313802, WO-A-9313808 or WO-A-9313809). It will be appreciated that the echogenicity of such microparticulate contrast agents may derive directly from the contained/associated gas and/or from gas (e.g. microbubbles) liberated from the solid material (e.g. upon dissolution of the microparticulate structure).

The disclosures of all of the above-described documents relating to gas-containing contrast agent formulations and their preparation are incorporated herein by reference; it will be appreciated that contrast agents according to the present invention may be prepared in similar manner by substituting an appropriate azeotropic gas mixture for the gases used in such prior art. The azeotropic mixture may itself be obtained by evaporation of a liquid mixture of the components. It is not necessary for the components of such a liquid mixture to be present in relative amounts corresponding to the ratio of components in the azeotropic gas mixture, since for a positive azeotropic system the lowest-boiling azeotropic mixture will inevitably boil off first from the liquid system regardless of its precise composition; where it initially differs from that of the azeotrope the composition of the remaining liquid mixture will accordingly change continually during boiling.

Gas microbubbles and other gas-containing materials such as microparticles preferably have an average size of 0.1–10 $\mu$m (e.g. 1–7 $\mu$m) in order to permit their free passage through the pulmonary system following administration, e.g. by intravenous injection, and to achieve resonance with preferred ultrasound imaging frequencies, typically 0.1–15 MHz.

Where phospholipid-containing compositions are employed in accordance with the invention, e.g. in the form of phospholipid-stabilised gas microbubbles, representative examples of useful phospholipids include lecithins (i.e. phosphatidylcholines), for example natural lecithins such as egg yolk lecithin or soya bean lecithin and synthetic or semisynthetic lecithins such as dimyristoylphosphatidylcholine, dipalmitoylphosphatidylcholine or distearoylphosphatidylcholine; phosphatidic acids; phosphatidylethanolamines; phosphatidylserines; phosphatidylglycerols; phosphatidylinositols; cardiolipins; sphingomyelins; fluorinated analogues of any of the foregoing; mixtures of any of the foregoing and mixtures with other lipids such as cholesterol. The use of phospholipids predominantly (e.g. at least 75%) comprising molecules individually bearing net overall charge, e.g. negative charge, for example as in naturally occurring (e.g. soya bean or egg yolk derived), semisynthetic (e.g. partially or fully hydrogenated) and synthetic phosphatidylserines, phosphatidylglycerols, phosphatidylinositols, phosphatidic acids and/or cardiolipins, may be particularly advantageous.

One useful method for the preparation of phospholipid-stabilised microbubbles of azeotropic gas mixtures comprises generating a dispersion of microbubbles of the gas mixture in an appropriate phospholipid-containing aqueous medium and subjecting the resulting dispersion to lyophilisation to yield a storage stable dried product which may be readily reconstituted in an aqueous medium to regenerate a microbubble dispersion. One or more agents with cryoprotective and/or lyoprotective effect and/or one or more bulking agents, for example an alcohol (e.g. an aliphatic alcohol such as t-butanol or a polyol such as glycerol), an aminoacid such as glycine, a carbohydrate (e.g. a sugar such as sucrose, mannitol, trehalose, glucose or lactose, a cyclodextrin or a polysaccharide such as dextran) or a polyglycol such as polyethylene glycol, may if desired be included in the initial dispersion, which may be prepared by any appropriate emulsion-generating technique, for example by sonication, shaking, high pressure homogenisation, high speed stirring or high shear mixing (e.g. with a rotor-stator homogeniser) of the phospholipid-containing medium in the presence of the desired azeotropic gas mixture. Aqueous media which may be used to reconstitute the dried product include water (especially sterile pyrogen-free water for injection), aqueous solutions such as saline (which may advantageously be balanced so that the final product for injection is not hypotonic), and aqueous solutions of one or more tonicity-adjusting substances such as salts (e.g. of plasma cations with physiologically tolerable counterions) or sugars, sugar alcohols, glycols and other non-ionic polyol materials (e.g. glucose, sucrose, sorbitol, mannitol, glycerol, polyethylene glycols, propylene glycols and the like).

Representative examples of gas-containing microparticulate matrix materials which may be useful in accordance with the invention include carbohydrates (for example hexoses such as glucose, fructose or galactose; disaccharides such as sucrose, lactose or maltose; pentoses such as arabinose, xylose or ribose; α-, β- and γ-cyclodextrins; polysaccharides such as starch, hydroxyethyl starch, amylose, amylopectin, glycogen, inulin, pulullan, dextran, carboxymethyl dextran, dextran phosphate, ketodextran, aminoethyldextran, alginates, chitin, chitosan, hyaluronic acid or heparin; and sugar alcohols, including alditols such as mannitol or sorbitol), inorganic salts (e.g. sodium chloride), organic salts (e.g. sodium citrate, sodium acetate or sodium tartrate), X-ray contrast agents (e.g. any of the commercially available carboxylic acid and non-ionic amide contrast agents typically containing at least one 2,4,6-triiodophenyl group having substituents such as carboxyl, carbamoyl, N-alkylcarbamoyl, N-hydroxyalkylcarbamoyl, acylamino, N-alkylacylamino or acylaminomethyl at the 3- and/or 5-positions, as in metrizoic acid, diatrizoic acid, iothalamic acid, ioxaglic acid, iohexol, iopentol, iopamidol, iodixanol, iopromide, metrizamide, iodipamide, meglumine iodipamide, meglumine acetrizoate and meglumine diatrizoate), and polypeptides and proteins (e.g. gelatin or albumin such as human serum albumin).

Ultrasound imaging modalities which may be used in accordance with the invention include two- and three-dimensional imaging techniques such as B-mode imaging (for example using the time-varying amplitude of the signal envelope generated from the fundamental frequency of the returned ultrasound pulse, from sub-harmonics or higher harmonics thereof or from sum or difference frequencies derived from the returned pulse and such harmonics, images generated from the fundamental frequency or the second harmonic thereof being preferred), colour Doppler imaging and Doppler amplitude imaging.

One aspect of this invention relates to the targeting of ultrasound contrast agents for disease imaging and drug delivery. Thus, a contrast agent comprising a halocarbon-containing azeotropic mixture in which the halocarbon has a molecular weight of at least 100 may be attached to one or more vector or drug molecules or a combination of both, where said vector(s) have affinity for a particular target site and/or structures within the body, e.g. for specific cells or areas of pathology or the vector or drug molecule may be linked to the contrast agent by one or more linkers connecting said reporter and vector(s).

The use of vectors to target specific areas of interest within the body is well-known in the art and their use will be routine to the skilled artisan. Suitable vectors of use in the present invention include protein and peptide vectors such as antibodies and the like.

The contrast agents of the invention can be coupled to one or more vectors either directly or through linking groups and may be linked to part of an encapsulating wall or matrix. The contrast agents may be connected directly to vectors such as monoclonal antibodies which recognise specific target areas. Alternatively, the contrast agents may be coupled to a secondary antibody which has a specificity for a primary antibody which in turn has specificity for a target area. Such use of secondary antibodies is advantageous in that appropriate selection of a secondary antibody allows the preparation of "universal" contrast agents which may be used for a wide range of applications since the primary antibody can be tailored to particular target areas.

Coupling of a contrast agent to a desired vector may be achieved by covalent or non-covalent means for example involving interaction with one or more functional groups located on the microbubble and/or vector. Examples of chemically reactive groups which may be employed for this purpose include amino, hydroxyl, sulfhydryl, carboxyl, and carbonyl groups, as well as carbohydrate groups, vicinal diols, thioethers, 2-aminoalcohols, 2-aminothiols, guanidinyl, imidazolyl and phenolic groups. The vector and contrast agents may also be linked by a linking group; many such groups are well-known in the art. Connection of the linker to the vector and microbubble may be achieved using routine synthetic chemical techniques.

Contrast agents in accordance with the invention may if desired be employed as delivery agents for bioactive moieties such as therapeutic drugs (i.e. agents having a beneficial effect on a specific disease in a living human or non-human animal), particularly to targeted sites. Thus, for example, therapeutic compounds may be present in the azeotropic gas mixture, may be linked to part of an encapsulating wall or matrix, e.g. through covalent or ionic bonds, if desired through a spacer arm, or may be physically mixed into such encapsulating or matrix material; this last option is particularly applicable where the therapeutic compound and encapsulating or matrix material have similar polarities or solubilities.

The therapeutic compound, which may if desired be coupled to a site-specific vector having affinity for specific cells, structures or pathological sites, may be released as a result of, for example, solubilisation of the encapsulating or matrix material, or disintegration of microbubbles or microparticles induced by ultra-sonication. Where a therapeutic agent is chemically linked to an encapsulating wall or matrix, the linkage or any spacer arm associated therewith may advantageously contain one or more labile groups which are cleavable to release the agent. Representative cleavable groups include amide, imide, imine, ester, anhydride, acetal, carbamate, carbonate, carbonate ester and disulphide groups which are biodegradable in vivo, e.g. as a result or hydrolytic and/or enzymatic action.

Representative and non-limiting examples of drugs useful in accordance with this embodiment of the invention include antineoplastic agents such as vincristine, vinblastine, vindesine, busulfan, chlorambucil, spiroplatin, cisplatin, carboplatin, methotrexate, adriamycin, mitomycin, bleomycin, cytosine arabinoside, arabinosyl adenine, mercaptopurine, mitotane, procarbazine, dactinomycin (antinomycin D), daunorubicin, doxorubicin hydrochloride, taxol, plicamycin, aminoglutethimide, estramustine, flutamide, leuprolide, megestrol acetate, tamoxifen, testolactone, trilostane, amsacrine (m-AMSA), asparaginase (L-asparaginase), etoposide, interferon a-2a and 2b, blood products such as hematoporphyrins or derivatives of the foregoing; biological response modifiers such as muramylpeptides; antifungal agents such as ketoconazole, nystatin, griseofulvin, flucytosine, miconazole or amphotericin B; hormones or hormone analogues such as growth hormone, melanocyte stimulating hormone, estradiol, beclomethasone dipropionate, betamethasone, cortisone acetate, dexamethasone, flunisolide, hydrocortisone, methylprednisolone, paramethasone acetate, prednisolone, prednisone, triamcinolone or fludrocortisone acetate; vitamins such as cyanocobalamin or retinoids; enzymes such as alkaline phosphatase or manganese superoxide dismutase; antiallergic agents such as amelexanox; anticoagulation agents such as phenprocoumon or heparin; circulatory drugs such as propranolol; metabolic potentiators such as glutathione; antituberculars such as p-aminosalicylic acid, isoniazid, capreomycin sulfate, cyclosexine, ethambutol, ethionamide, pyrazinamide, rifampin or streptomycin sulphate; antivirals such as acyclovir, amantadine, azidothymidine, ribavirin or vidarabine; blood vessel dilating agents such as diltiazem, nifedipine, verapamil, erythritol tetranitrate, isosorbide dinitrate, nitroglycerin or pentaerythritol tetranitrate; anticoagulants such as warfarin or heparin; antibiotics such as dapsone, chloramphenicol, neomycin, cefaclor, cefadroxil, cephalexin, cephradine, erythromycin, clindamycin, lincomycin, amoxicillin, ampicillin, bacampicillin, carbenicillin, dicloxacillin, cyclacillin, picloxacillin, hetacillin, methicillin, nafcillin, penicillin or tetracycline; antiinflammatories such as diflunisal, ibuprofen, indomethacin, meclefenamate, mefenamic acid, naproxen, phenylbutazone, piroxicam, tolmetin, aspirin or salicylates; antiprotozoans such as chloroquine, metronidazole, quinine or meglumine antimonate; antirheumatics such as penicillamine; narcotics such as paregoric; opiates such as codeine, morphine or opium; cardiac glycosides such as deslaneside, digitoxin, digoxin, digitalin or digitalis; neuromuscular blockers such as atracurium mesylate, gallamine triethiodide, hexafluorenium bromide, metocurine iodide, pancuronium bromide, succinylcholine chloride, tubocurarine chloride or vecuronium bromide; sedatives such as amobarbital, amobarbital sodium, apropbarbital, butabarbital sodium, chloral hydrate, ethchlorvynol, ethinamate, flurazepam hydrochloride, glutethimide, methotrimeprazine hydrochloride, methyprylon, midazolam hydrochloride, paraldehyde, pentobarbital, secobarbital sodium, talbutal, temazepam or triazolam; local anaesthetics such as bupivacaine, chloroprocaine, etidocaine, lidocaine, mepivacaine, procaine or tetracaine; general anaesthetics such as droperidol, etomidate, fentanyl citrate with droperidol, ketamine hydrochloride, methohexital sodium or thiopental and pharmaceutically acceptable salts (e.g. acid addition salts such as the hydrochloride or hydrobromide or base salts such as sodium, calcium or magnesium salts) or derivatives (e.g. acetates) thereof. Other examples of therapeutics include genetic material such as nucleic acids, RNA, and DNA of natural or synthetic origin, including recombinant RNA and DNA. DNA encoding certain proteins may be used in the treatment of many different types of diseases. For example, tumor necrosis factor or interleukin-2 may be provided to treat advanced cancers; thymidine kinase may be provided to treat ovarian cancer or brain tumors; interleukin-2 may be provided to treat neuroblastoma, malignant melanoma or kidney cancer; and interleukin-4 may be provided to treat cancer.

The following non-limitative Examples serve to illustrate the invention.

Preparation 1
Preparation of azeotropic gas mixtures
a) Perfluoro-n-pentane: n-pentane azeotrope 4.59 g (0.016 mol) of perfluoro-n-pentane (b.p. 28° C.) and 0.99 g (0.014 mol) of n-pentane (b.p. 36°) were mixed in a vial and one or two ceramic boiling aids were added. The resulting mixture boiled at the room temperature of ca. 22° C. According to Simons et al. in *J. Chem. Phys* 18(3) (1950), pp. 335–346 the resulting azeotropic gas mixture contains approximately equimolar amounts of the two components.

b) Perfluoro-n-hexane: n-pentane azeotrope

The procedure of Preparation 1(a) was repeated using 4.71 g (0.014 mol) of perfluoro-n-hexane (b.p. 59° C.) and 0.89 g (0.012 mol) of n-pentane. The resulting mixture boiled readily at 35° C. but not at room temperature, indicating an azeotropic boiling point between these temperatures.

c) Perfluoro-4-methylpent-2-ene: n-pentane azeotrope

The procedure of Preparation 1(a) was repeated using 4.05 g (0.014 mol) of perfluoro-4-methylpent-2-ene (b.p. 49° C.) and 1.01 g (0.014 mol) of n-pentane. The resulting mixture boiled at ca. 25° C.

Preparation 2
Aqueous phospholipid dispersion 5.02 g of 85% glycerol, 1.50 g of propylene glycol and 102 g of water were mixed to give a homogeneous solution. 99.5 mg of hydrogenated phosphatidylserine were added to a 20 ml portion of this solution and the resulting mixture was heated to 80° C. for ca. 5 minutes using a water bath and then allowed to cool to room temperature prior to use.

EXAMPLE 1

Phospholipid-stabilised dispersion of perfluoro-n-pentane: n-pentane azeotrope

A 1 ml portion of the phospholipid dispersion from Preparation 2 was transferred to a 2 ml chromatography vial which was then placed for ca. 1 hour in a heated cabinet maintained at 37° C. An azeotropic gas mixture of perfluoro-n-pentane and n-pentane was obtained by heating a liquid mixture prepared as in Preparation 1(a) to 37° C., and this gas was introduced into the headspace of the heated vial. The vial was then immediately capped and shaken at 37° C. for 45 seconds using an Espe CapMix® mixer for dental materials, yielding a milky white dispersion which was characterised by microscopy both immediately and after storage for 3 days at 37° C. The microscopy images showed a highly concentrated dispersion of microbubbles with sizes between 1 and 5 µm.

EXAMPLE 2

Phospholipid-stabilised dispersion of perfluoro-n-hexane: n-pentane azeotrope

A 1 ml portion of the phospholipid dispersion from Preparation 2 was transferred to a 2 ml chromatography vial which was then placed for ca. 1 hour in a heated cabinet maintained at 37° C. An azeotropic gas mixture of perfluoro-n-hexane and n-pentane was obtained by heating a liquid mixture prepared as in Preparation 1(b), by application of hot tap water, and this gas was introduced into the headspace of the heated vial. The vial was then immediately capped and shaken at 37° C. for 45 seconds using an Espe CapMix® mixer for dental materials, yielding a turbid dispersion which was characterised by microscopy both immediately and after storage for 4 days at 37° C. The microscopy images showed a microbubble dispersion wherein a fraction of the microbubbles had sizes between 5 and 10 µm.

EXAMPLE 3

Phospholipid-stabilised dispersion of perfluoro-4-methylpent-2-ene: n-pentane azeotrope A 1 ml portion of the phospholipid dispersion from Preparation 2 was transferred to a 2 ml chromatography vial which was then placed for ca. 1 hour in a heated cabinet maintained at 37° C. An azeotropic gas mixture of perfluoro-4-methylpent-2-ene and n-pentane was obtained by heating a liquid mixture prepared as in Preparation 1(c), by application of hot tap water, and this gas was introduced into the headspace of the heated vial. The vial was then immediately capped, allowed to rest at 37° C. for ca. 30 minutes and then shaken at 37° C. for 45 seconds using an Espe CapMix® mixer for dental materials, yielding a turbid dispersion which was characterised by microscopy both immediately and after storage for 4 days at 37° C. The microscopy images showed a microbubble dispersion wherein a fraction of the microbubbles had sizes between 5 and 10 µm.

What is claimed is:

1. A contrast agent for use in diagnostic studies comprising a dispersion in an injectable aqueous medium of a biocompatible azeotropic mixture which is in gaseous form at 37° C., characterised in that at least one component of said mixture is a halocarbon having a molecular weight of at least 100.

2. A contrast agent as claimed in claim 1 wherein said halocarbon comprises at least one fluorine atom.

3. A contrast agent as claimed in claim 1 wherein said halocarbon is a perfluorocarbon.

4. A contrast agent as claimed in claim 3 wherein said perfluorocarbon is a perfluorobutane, a perfluoropentane, a perfluorohexane or perfluoro-4-methylpent-2-ene.

5. A contrast agent as claimed in claim 1 wherein said azeotropic mixture comprises an unsubstituted hydrocarbon.

6. A contrast agent as claimed in claim 5 wherein said hydrocarbon is n-pentane.

7. A contrast agent as claimed in claim 1 wherein said azeotropic mixture is stabilised by amphiphilic lipid material.

8. A contrast agent as claimed in claim 7 wherein said amphiphilic lipid material comprises a membrane-forming lipid.

9. A contrast agent as claimed in claim 8 wherein said membrane-forming lipid comprises a phospholipid.

10. A contrast agent as claimed in claim 9 wherein at least 75% of said membrane-forming lipid comprises a negatively charged phospholipid.

11. A contrast agent as claimed in claim 10 wherein said negatively charged phospholipid comprises at least one phosphatidylserine.

12. A method of generating enhanced ultrasound images of a human or non-human animal subject which comprises the steps of:
   i) injecting an ultrasound contrast agent as claimed in claim 1; and
   ii) generating an ultrasound image of at least a part of said subject.

* * * * *